US009383348B2

(12) United States Patent
Repine

(10) Patent No.: US 9,383,348 B2
(45) Date of Patent: Jul. 5, 2016

(54) COMPOSITIONS AND METHODS FOR TREATING LUNG DISORDERS

(75) Inventor: John E. Repine, Denver, CO (US)

(73) Assignee: John E. Repine, Aurora, CO (US)

( * ) Notice: Subject to any disclaimer, the term of this patent is extended or adjusted under 35 U.S.C. 154(b) by 315 days.

(21) Appl. No.: 13/000,603

(22) PCT Filed: Jun. 22, 2009

(86) PCT No.: PCT/US2009/003704
§ 371 (c)(1),
(2), (4) Date: Mar. 21, 2011

(87) PCT Pub. No.: WO2009/154800
PCT Pub. Date: Dec. 23, 2009

(65) Prior Publication Data
US 2011/0160268 A1    Jun. 30, 2011

Related U.S. Application Data

(60) Provisional application No. 61/074,626, filed on Jun. 21, 2008.

(51) Int. Cl.
| *A61K 8/00* | (2006.01) |
| *A61K 31/4178* | (2006.01) |
| *A61K 31/00* | (2006.01) |
| *A61K 31/195* | (2006.01) |
| *G01N 33/50* | (2006.01) |
| *A61K 31/385* | (2006.01) |
| *A61K 31/4164* | (2006.01) |

(52) U.S. Cl.
CPC .......... *G01N 33/5005* (2013.01); *A61K 31/195* (2013.01); *A61K 31/385* (2013.01); *A61K 31/4164* (2013.01); *G01N 2500/10* (2013.01); *G01N 2800/12* (2013.01); *G01N 2800/125* (2013.01)

(58) Field of Classification Search
USPC ............................................ 514/359, 1.5, 92
See application file for complete search history.

(56) References Cited

FOREIGN PATENT DOCUMENTS

WO    WO 93/21946    11/1993    ............. A61K 37/02

OTHER PUBLICATIONS

Matthay et al., "Acute Lung Injury and the Acute Respiratory Distress Syndrome", Am. J. Respir. Cell. Mol. Biol, 2005, 33, 319-327.*
Schneeberger-Kelley et al., J Cell Biol. Jun. 1, 1968; 37(3): 781-793.*
Bernard et al., Chest, 1997, 112, 164-172.*
Taber's Medical Dictionary Online, http://www.tabers.com/tabersonline/view/Tabers-Dictionary/738506/all/adult_respiratory_distress_syndrome.*
American Thoracic Society, Chapter 2, http://www.thoracic.org/education/breathing-in-america/resources/chapter-2-acute-respiratory-distress-syndrome.pdf.*
Windsor et al. ("Windsor", Brit. J. Surgery, 2005, 80, 10-17).*
Bhatia et al. ("Bhatia", J. Pathol, 2004, 202, 145-156).*
Vazin et al. ("Vazin", Int. J. of Pharmacology, 2005, 1, 9-16).*
International Search Report and Written Opinion issued Jan. 6, 2011, in PCT Application No. PCT/US2009/003704.
Omer Sakrak et al., "Ergothioneine Modulates Proinflammatory Cytokines and Heat Shock Protein 70 in Mesenteric Ischemia and Reperfusion Injury", Journal of Surgical Research, 144:36-42 (2008).
Irfan Rahman et al., "Ergothioneine inhibits oxidative stress- and TNF-α-induced NF-κB activation and interleukin-8 release in alveolar epithelial cells", Biochemical and Biophysical Research Communications, 302:860-864 (2003).
Robert M. Strieter et al., "Acute Lung Injury: The Role of Cytokines in the Elicitation of Neutrophils", Journal of Investigative Medicine, 42(4):640-651 (1994).
Bernard et al., Clinical Investigations in Critical Care, "A Trial of Antioxidants N-acetylcysteine and Procysteine in the ARDS", CHEST, 112:164-172 (Jul. 1997).
Dunhill, "The Pathology of Asthma, with Special Reference to Changes in the Bronchial Mucosa", J. Clin. Path., 13:27-33 (1960).
Galani et al., "The role of apoptosis in the pathophysiology of Acute Respiratory Distress Syndrome (ARDS) An up-to-date cell-specific review", Pathology—Research and Practice, 206:145-150 (2010).
Kang et al., "Bloodstream infections in adult patients with cancer: clinical features and pathogenic significance of *Staphylococcus aureus* bacteremia", Support Care Cancer, 20:2371-2378 (2012).
Rahman et al., "Ergothioneine inhibits oxidative stress- and TNF-alpha-induced NF-κB activation and interleukin-8 release in alveolar epithelial cells". Biochemical and Biophysical Research Communication, 302:860-864 (2003).
Schneeberger-Keeley et al., "The Ultrastructural Basis of Alveolar-Capillary Membrane Permeability to Peroxidase Used as a Tracer", The Journal of Cell Biology, 37:781-793 (1968).
Tomashefski, Jr., "Pulmonary pathology of acute respiratory distress syndrome", Clin. Chest Med., 3:435-66 (Sep. 21, 2000) (Abstract only).
Chang et al., "Causes of Death in Adults with Acute Leukemia", Medicine (Baltimore), 55(3):259-268 (1976).
Gonzalez-Lopez et al., "Repair after acute lung injury: molecular mechanisms and therapeutic opportunities", Critical Care, 16:209-216 (2012).
Hogg et al., "The Pathology of Chronic Obstructive Pulmonary Disease", Annu. Rev. Pathol., 4:435-459 (2009).
Jeffrey, P.K., "Pathology of asthma", Br. Med. Bull., 4823-39 (1992).
Mayo Clinic Staff, "Diseases and Conditions", ARDS, http://www.mayoclinic.org/diseases-conditions/ards/basics/definition/con-20030070, (2011).

(Continued)

*Primary Examiner* — Peter J Reddig
*Assistant Examiner* — Kauser Akhoon
(74) *Attorney, Agent, or Firm* — Morgan Lewis & Bockius LLP

(57) ABSTRACT

The present invention relates to methods of treating subjects with alveolar capillary membrane injury or methods of preventing alveolar capillary membrane injury in subjects, with the methods comprising administering to the subjects a therapeutically effective amount of ergothioneine and a pharmaceutically acceptable carrier. The invention also relates to methods of screening candidate compounds for their ability to mitigate the effects of alveolar capillary membrane injury.

14 Claims, 5 Drawing Sheets

(56) References Cited

OTHER PUBLICATIONS

Rosiglitazone, http://en.wikipedia.org/wiki/rosiglitazone, (2014).

Sessler et al., "Are Corticosteroids Useful in Late-Stage Acute Respiratory Distress Syndrome?", Respiratory Care, 55(1):43-55 (2010).

Steinberg et al., "Efficacy and Safety of Corticosteroids for Persistent Acute Respiratory Distress Syndrome", New England Journal of Medicine, 354:1671-1784 (2006).

Summerhill, E.M., "Interstitial (Nonidiopathic) Pulmonary Fibrosis", http://emedicine.medscape.com/article/301337—overview, (2011).

Thompson et al., "Steroid treatment for persistent ARDS: a word of caution", Critical Care, 11(6):425 (2007).

Three Phases of ARDS, ARDS and MODS, http://modsandards.blog.com/2010101 /injury-or-exudative-phase. html., (Jan. 27, 2010).

Wu et al., "IL-23-dependent IL-17 production is essential in neutrophil recruitment and activity in mouse lung defense against respiratory Mycoplasma pneumoniae infection", Microbes and Infection, 9:78-86 (2007).

\* cited by examiner

COMPOSITIONS AND METHODS FOR TREATING LUNG DISORDERS

CROSS-REFERENCE TO RELATED APPLICATIONS

This application is a 371 filing based on PCT/US2009/003704, filed Jun. 22, 2009, which claims priority to U.S. Provisional Application No. 61/074,626, filed Jun. 21, 2008, both of which are hereby incorporated by reference in their entirety.

STATEMENT REGARDING FEDERALLY SPONSORED RESEARCH OR DEVELOPMENT

This invention was made with government support under Grant No. RO1-HL-45582 awarded by the National Institutes of Health The government has certain rights in the invention.

BACKGROUND OF THE INVENTION

1. Field of the Invention

The present invention relates to methods of treating subjects with alveolar capillary membrane injury or methods of preventing alveolar capillary membrane injury in subjects, with the methods comprising administering to the subjects a therapeutically effective amount of ergothioneine and a pharmaceutically acceptable carrier. The invention also relates to methods of screening candidate compounds for their ability to mitigate the effects of alveolar capillary membrane injury.

2. Background of the Invention

Exposure to various insults frequently leads to alveolar capillary membrane injury (ACMI), which can result in such syndromes as Acute Respiratory Distress Syndrome (ARDS) and Acute Lung Injury (ALI). The alveolar capillary membrane is simply the thin tissue barrier between the alveolar sacs of the lungs and the pulmonary capillaries through which gases are exchanged. In addition, the alveolar capillary membrane is actively involved in solute and fluid flux between the alveolar surface, interstitium and the blood, as well as fluid clearance from the alveolar spaces to the interstitial spaces. See Gauzzi, M., *Chest,* 124(3): 1090-1102 (2003), incorporated by reference.

ARDS, the most severe form of ALI, is an often fatal, non-cardiogenic, acute, usually diffuse, edematous, hemorrhagic and/or inflammatory lung injury. For unknown reasons, ARDS can complicate infection, trauma, hyperoxia, radiation, hemorrhage, blast exposure, chemical exposure, pancreatitis, brain injury, smoke inhalation, transfusions, drug reactions and many other predisposing disorders including infection by CDC Category A-C pathogens. Individuals who sustain any of the predisposing disorders or conditions such as those listed above are considered to be at-risk for developing ALI and ARDS. See Repine, J. E., *Lancet* 339: 466-469, (1992) and Ware, L. B. and Matthay, M. A., *New Engl. J. Med.* 29:2788-2796 (2005), both of which are incorporated by reference. ARDS often leads to multiple organ failure (MOF) and death. ARDS survivors also develop inexplicably develop post-traumatic stress disorder (Davydow), severe muscle weakness (Herridge) and other continuing disabilities with long-term consequences.

After initial injury of the alveolar capillary membrane, the progression to ALI and/or ARDS is unclear, but it appears to involve a cytokine triggered inflammation and oxidative stress involving mononuclear phagocytes (MNP), neutrophils (PMN) and xanthine oxidoreductase (XOR). ARDS patients and ARDS animal models have increased lung and blood cytokine levels, e.g., IL-1, IFN-γ, TNF-α and IL-8 and increased lung MNP, PMN and XOR levels, as well as deficiencies in lung glutathione (GSH) levels. See Repine (*Lancet,* 1992), Ware (*New Engl. J. Med.,* 2005) and Bernard, G. R., et al., *Chest,* 112: 164-172 (1997). NF-κB is also activated in lungs and MNP of ARDS patients. Additionally, lipid peroxidation and carbonyl protein levels are generally increased in ARDS patients. Patients and animals with ARDS also exhale more hydrogen peroxide ($H_2O_2$). See Baldwin, S. R., et al., *Lancet* 1, 11-14 (1986) and Leff, J. A., et al., *Am. J. Physiol.* 265:L501-L506 (1993), both of which are incorporated by reference. While not especially toxic intrinsically, $H_2O_2$ often quickly forms highly toxic by-products, most notably a hydroxyl radical (.OH), produced by iron-catalyzed Fenton chemistry, hypochlorous acid. (HOCL) produced by reaction with myeloperoxidase (MPO)—a neutrophil component—and perhaps singlet molecular oxygen ($^1O_2$). The latter reactive species have appreciable toxicity and readily damage endothelial, epithelial and other cells in vitro.

Current treatments of ARDS are limited to physical treatments, such as ventilation, and there are currently no pharmaceutical therapies available that treat or remedy the root cause of ALI, ARDS or other syndromes associated with the development or acute or chronic consequences of alveolar capillary membrane injury. Indeed, according to the National Heart Lung and Blood Institute of the National Institutes of Health, the only medicinal treatments available for treatment of ARDS at this time appear to be limited to anti-infectives used for treating the pathogen infection and agents which provide supportive care, relieve pain or discomfort. See the world wide web at: nhlbi.nih.gov/health/dci/Diseases/Ards/Ards_WhatIs.html. In addition, ARDS is recognized as a disease that is extremely difficult to treat once it has started and become "established." Mechanical ventilation is often associated with complications such as ventilator-associated pneumonia and ventilator-associate lung injury. These complications lead to significant morbidity in ALI and ARDS patient populations. Therefore, a treatment is needed that is effective, and not potentially harmful, even when given after exposure to an ARDS-inciting insult and after ARDS has started. At present, no such post-ARDS development therapy exists. Thus, there is a major need for the provision of the safe and effective treatment of alveolar capillary membrane injury.

Antioxidant defense may be pursued as a strategy for limiting the alveolar toxicity of reactive oxygen species associated with ALI and ARDS. Combating the effects of reactive oxygen species was once a promising area of study for those looking to limit the severity of, or potentially prevent, ALI and ARDS. While, N-acetylcysteine (NAC) and L-2-oxothiazolidine-4-carboxylate (Procysteine) have been most extensively studied, the results of human studies comparing NAC to placebo have been underwhelming. These unsatisfactory trials have led to little enthusiasm for conducting ongoing studies of antioxidant defense strategies for the treatment of ARDS. see Mark D. Siegel, MD, *Novel therapies for the acute respiratory distress syndrome*, UpToDate (Jan. 6, 2009 update), which is available on the world wide web at www.uptodate.com/online/content/topic.do?topicKey=cc_medi/18425&selectedTitle=5~150 &source=search_result#22.

Similarly, a prophylactic therapy is also needed, such that the preventative could be given safely to individuals exposed to a potential insult before they develop ARDS. It is a particular need to have such a treatment readily available for use in the event of a mass casualty such as an explosive blast, a radiological insult, a toxic chemical exposure, inhalation of toxic fumes from fires or the like that could result in a large scale need for effective prevention or treatment of ARDS. At present, no such post-exposure (but pre-ARDS development) therapy exists. Accordingly, finding an ARDS therapy that was protective and/or useful in treating ongoing ARDS would be a new discovery. It is anticipated that ways will be developed to increase the ability to predict which at-risk individuals are more likely to develop ARDS and this information would then be used to institute therapies that can prevent ALI and ARDS development.

SUMMARY OF THE INVENTION

The present invention relates to methods of treating subjects with alveolar capillary membrane injury, with the methods comprising administering to the subjects a therapeutically effective amount of ergothioneine (in either the L- and/or D-form) and a pharmaceutically acceptable carrier.

The present invention also relates to methods of reducing the risk of subjects developing alveolar capillary membrane injury, with the methods comprising administering to the subjects a therapeutically effective amount of ergothioneine and a pharmaceutically acceptable carrier, with the administration being prior to the onset of an insult that results in alveolar capillary membrane injury.

The present invention also relates to methods of reducing the severity and consequences of ongoing alveolar capillary membrane injury, with the methods comprising administering to the subjects a therapeutically effective amount of ergothioneine and a pharmaceutically acceptable carrier, with the administration being after the onset of an insult and the development of signs and/or symptoms that result from alveolar capillary membrane injury.

The present invention also relates to methods of screening candidate compounds for their ability to mitigate the effects of alveolar capillary membrane injury. The screening methods comprise stimulating a control and experimental population of cells or animal models of alveolar capillary membrane injury in the presence of either ergothioneine or the candidate compound, with the stimulus being capable of producing markers associated with or reflecting inflammatory acute lung injury in the two groups of cells or animal models. Any reduction in the markers of inflammatory acute lung injury in the experimental group of cells or animals would indicate that the candidate compound may be useful for mitigating the effects of alveolar capillary membrane injury.

DETAILED DESCRIPTION OF THE INVENTION

Figure 1A:
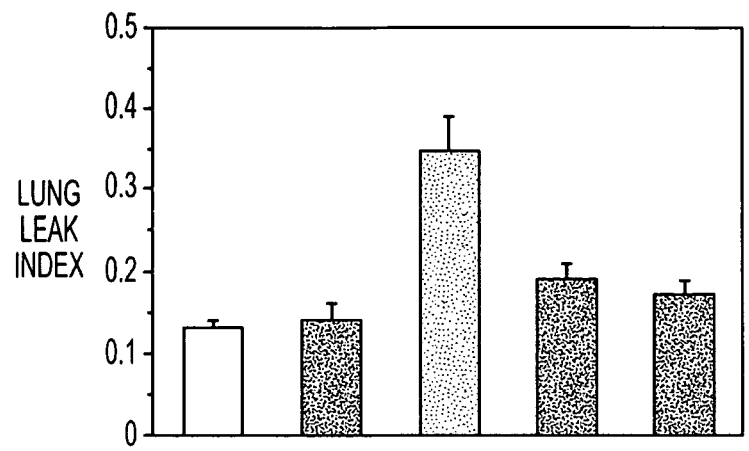
FIG. 1 depicts the ability of N-acetylcysteine (NAC) to mitigate or prevent inflammatory acute lung injury mediated by interleukin 1 (IL-1).

The present invention relates to methods of treating subjects with alveolar capillary membrane injury (ACMI). The phrase "alveolar capillary membrane injury" is intended to mean a condition whereby the alveolar capillary membrane of a subject has reduced function. As mentioned above, the alveolar capillary membrane in a subject is the thin tissue barrier between the alveolar sacs of the lungs and the pulmonary capillaries through which gases are exchanged. In addition, the alveolar capillary membrane is actively involved in solute and fluid flux between the alveolar surface, interstitium and the blood, as well as fluid clearance from the alveolar spaces to the interstitial spaces. See Gauzzi, M., Chest, 124 (3): 1090-1102 (2003), incorporated by reference. Once injured, the alveolar capillary membrane may lose its ability to efficiently conduct gas exchange, fluid regulation and/or properly control inflammatory and vascular reactivity responses. The injury may result in the complete incapacity of the membrane to conduct gas exchange and/or fluid regulation, or the injury may result in a reduction, but not total ablation, of the ability of the membrane to conduct gas exchange and/or fluid regulation. The injury may also result in a significant decrease in lung compliance. The treatments described herein, therefore, may increase the capacity of the injured alveolar membrane or it may completely restore lung compliance and the ability the membrane to conduct gas exchange and/of fluid regulation. Moreover, the treatments described herein may act upon either the gas exchange conductance properties of the membrane or the fluid regulating properties of the membrane, or both.

The methods of the present invention can be used to treat any condition or syndrome involving alveolar capillary membrane injury. Examples of syndromes or conditions involving alveolar capillary injury include, but are not limited to, acute lung injury (ALI), acute respiratory disorder syndrome (ARDS) infant respiratory distress syndrome (IRDS), post-traumatic stress disorder (PTSD), traumatic brain injury and neurogenic pulmonary edema (NPE). ACMI can sometimes accompany injuries to the brain, PNE and in PTSD. As used herein, the term "treatment" is used to indicate a procedure which is designed ameliorate one or more causes, symptoms, or untoward effects of the alveolar capillary membrane injury in a subject. Likewise, the term "treat" is used to indicate performing a treatment. The treatment can, but need not, cure the subject, i.e., remove the cause(s), or remove entirely the symptom(s) and/or untoward effect(s) of the abnormal condition in the subject. Thus, a treatment may include treating a subject to attenuate symptoms of the injury such as, but not limited to, shortness of breath, tachypnea and low blood pressure, or may include removing or decreasing the severity of the root cause of the abnormal condition or injury in the subject. The treatment might also reduce signs of alveolar capillary membrane injury such as hypoxia, lung and systemic inflammatory and oxidative stress responses that contribute to other organ dysfunction (multiple organ failure). As used herein, the term "subject" is used interchangeably with the term "patient," and is used to mean an animal, in particular a mammal, and even more particularly a non-human or human primate.

The alveolar capillary membrane injury may be caused by any insult or injury that is capable of damaging the membrane's ability to conduct gas exchange and/or fluid regulation. Examples of underlying conditions that may result in ACMI include, but are not limited to, sepsis, pulmonary infection, e.g., pneumonia, shock, e.g., hemorrhagic shock, lung trauma, chronic heart failure (CHF), drug overdose, e.g., tricyclic anti-depressant overdose, transfusions, salt water inhalation, noxious gas or smoke inhalation, radiation etc. Regardless of the root cause the membrane injury, the methods of the present invention can be used to treat or prevent the injury to the membrane.

The ACMI is treated by administering to the subject a therapeutically effective amount of ergothioneine and a pharmaceutically acceptable carrier. In one embodiment, the egothioniene is L-ergothioneine. In another embodiment, the egothioniene is D-ergothioneine. In one embodiment, the egothioniene is a racemic mixture of L-ergothioneine. As used herein, the term "administer" and "administering" is intended to mean are used to mean introducing at least one compound into a subject. When administration is for the purpose of treatment, the substance is provided at, or after the onset of, a symptom or sign of the membrane injury. As used herein, a "symptom" is a subjective manifestation from the point of view of the patient, e.g., shortness of breath. A "sign," on the other hand, is an objective, clinical manifestation that is often times measurable or quantifiable, e.g., low blood oxygen levels. The therapeutic administration of this substance serves to attenuate any symptom or sign, or prevent additional symptoms or signs from arising. When administration is for the purposes of preventing membrane injury ("prophylactic administration" or "pre-treatment"), the substance is provided in advance of any visible or detectable symptom or sign of ACMI, or prior to the onset of an insult that results in alveolar capillary membrane injury. The prophylactic administration of the substance serves to attenuate subsequently arising symptoms or signs or prevent symptoms or signs from arising altogether. For example, ergothioneine will be administered intravenously in ICUs to individuals who are "at-risk" because of predisposing conditions and/or who have ALI or ARDS. In addition, oral administration could be used for mass casualty situations in which ergothioneine is given by first responders to individuals exposed to an insult as a matter of course.

The route of administration of the compound includes, but is not limited to, topical, transdermal, intranasal, transmucosal, vaginal, rectal, oral, subcutaneous, intravenous, intraarterial, intramuscular, intraosseous, intraperitoneal, epidural and intrathecal.

As discussed above, the methods of the present invention also relate to methods of preventing alveolar capillary membrane injury in a subject. As used herein, the term "prevent" is synonymous with "reducing the risk" such that "prevention" is not intended to be an absolute term that would guarantee the subject from acquiring ACMI or exhibiting symptoms thereof. Rather, "prevention" is intended to mean that the pre-treated subject has a reduced risk of ACMI or exhibiting symptoms or signs of ACMI, over a subject that has not been pre-treated. "Reducing the risk" means that the pre-treated subjects exhibit attenuated symptoms or signs of ACMI or that the symptoms of ACMI have a reduced severity over the non-pre-treated subjects. As used herein, a "decreased risk" or a "reduced risk" also means that the pre-treated subject has a reduced chance of developing or acquiring the ACMI or exhibiting at least one symptom or sign of ACMI compared to a subject without pre-treatment. Determining risk or chance is a matter of routine statistical analysis well known in the art.

The treatment and prevention methods of the present invention comprise administering a therapeutically effective amount of ergothioneine to subjects in need thereof. In one embodiment, the administered egothioneine is L-ergothioneine. In another embodiment, the administered egothioneine is D-ergothioneine. In another embodiment, the administered egothioneine is a racemic mixture of L-ergothioneine. As used herein, the term ergothioneine, without reference to a specific isomer, can mean the L-isomer, the D-isomer or a racemic mixture of both the L- and D-isomers. Ergothioneine (ERGO) is a unique, naturally occurring antioxidant which is abundant in most plants and animals. ERGO exists in many tissues but is concentrated in tissues which are exposed to a high degree of oxidative stress such as RBC, lens, seminal fluid, kidney, lung and liver. Similar in many respects to glutathione (GSH), ERGO protects tissues against oxidative stress. ERGO can prevent singlet molecular oxygen ($^1O_2$) formation, chelate iron and other metal ions and activate glutathione peroxidase (GPX) and glutathione reductase (GRX). ERGO can also scavenge hydrogen peroxide ($H_2O_2$), hypochlorous acid (HOCL) and hydroxyl radicals (OH) at least in vitro. Since neutrophils are a major source of HOCL, ERGO may also protect cells from neutrophil-induced damage. ERGO also inhibits peroxynitrite (ONOO—) mediated nitration of tyrosine (and presumably other amino acids) and ONOO— induced inactivation of α-1-protease inhibitor. ERGO treatment protects rats against lipid peroxide associated hepatic injury and counteracts the toxicity of $H_2O_2$ to spermatozoa viability and survival. The latter protection reportedly occurs because ERGO accelerates GSH redox pathways.

In specific embodiments of the present invention, the methods comprise administering derivatives of L-ergothioneine in lieu of, or in addition to (co-administration), L-erothioneine. As used herein, derivatives of ERGO include, but are not limited to, those compounds comprising a 2-mercaptoimidizole ring, which are described in U.S. Pat. No. 6,056,965, the entirety of which is incorporated by reference. In another embodiment, the methods of the present invention comprise administering or co-administering prodrugs of the active compounds. As used herein, a "prodrug" is a compound that a biological system metabolizes to an active compound as a result of spontaneous chemical reaction(s), enzyme catalyzed chemical reaction(s), and/or metabolic chemical reaction(s), or a combination of each. Standard prodrugs are formed using groups attached to functionality, e.g., HO—, HS—, HOOC—, $R_2N$—, associated with the drug, that cleave in vivo. Standard prodrugs include, but are not limited to, carboxylate esters where the group is alkyl, aryl, aralkyl, acyloxyalkyl, alkoxycarbonyloxyalkyl as well as esters of hydroxyl, thiol and amines, where the group attached is an acyl group, an alkoxycarbonyl, aminocarbonyl, phosphate or sulfate. The groups illustrated are exemplary and not exhaustive, and one skilled in the art could prepare other known varieties of prodrugs. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc.

As mentioned above, one embodiment the treatment and prevention methods comprise co-administering ergothioneine with at least one additional compound. The term "co-administer" indicates that each of at least two compounds is administered during a time frame wherein the respective periods of biological activity or effects overlap. Thus, the term "co-administer" includes sequential as well as coextensive administration of the compounds of the present invention. And similar to "administering," "co-administration" of more than one substance can be for either therapeutic and/or prophylactic purposes. If more than one substance is co-administered, the routes of administration of the two or more substances need not be the same. The scope of the invention is not limited by the identity of the substance which may be co-administered. In one specific embodiment, L-ergothioneine is co-administered with a derivative of L-ergothioneine, N-acetylcysteine (NAC), an organoselenium, a thiol-yielding compound, a glutathione enhancing compound and/ok alpha-lipoic acid. Examples of organoselenium compounds include, but are not limited to those compounds disclosed in U.S. Pat. No. 6,525,040, which is incorporated by reference. A thiol-yielding compound is any compound that, when administered, results in an increase in the amount or activity of glutathione redox cycle activity. In another specific embodiment, D-ergothioneine is co-administered with a derivative of L-ergothioneine or D-ergothioneine, N-acetylcysteine (NAC) and/or alpha-lipoic acid. In yet another specific embodiment, a racemic mixture of ergothionine is co-administered with a derivative of L-ergothioneine or D-ergothioneine, N-acetylcysteine (NAC) and/or alpha-lipoic acid. In a more specific embodiment, L-ERGO is administered prior to the administration D-ERGO. In another more specific embodiment, D-ERGO is administered prior to the administration L-ERGO. In another embodiment, the ERGO is administered prior to the administration of the second compound, e.g., NAC. In another more specific embodiment, L-ERGO is administered prior to the administration D-ERGO and/or another compound, e.g., NAC. In yet another more specific embodiment, D-ERGO is administered prior to the administration L-ERGO and/or another compound, e.g., NAC. In another specific embodiment, the ERGO is administered after the administration of the second compound, e.g., NAC. In another more specific embodiment, L-ERGO is administered after the administration D-ERGO and/or another compound, e.g., NAC. In yet another more specific embodiment, D-ERGO is administered after the administration L-ERGO and/or another compound, e.g., NAC. In yet another embodiment, the second compound, e.g., NAC, is administered at the same time as the ERGO. Other compounds that may be co-administered include, but are not limited to, anti-inflammatory agents, antioxidants, anti-infectives, agents which impair clotting mechanisms, agents that alters GSH levels or GSH redox cycle activity and agents that decrease NF-kB activity. As one of skill in the art will recognize, the sequence of administration can be altered for the ERGO and the additional compound(s) being administered.

Both NAC and ERGO target and can correct a fundamental pathophysiologically meaningful common abnormality (GSH deficiency and oxidative stress) that occurs universally in ARDS patients. Accordingly, regardless of the specific insult, NAC and ERGO/or treatment should be beneficial in ARDS. This concept distinguishes from other strategies which may be directed at counteracting a single unique organism, such as Ebola virus. The basic nature of the invention also means that NAC and/or ERGO treatment might abrogate ARDS produced by new emerging and undefined pathogens which have naturally or purposefully been modified genetically.

The invention offers the possibility of broad spectrum interventions that will also be effective against every insult that leads to ARDS. A wide variety of chemical, traumatic, blast, infectious, hyperoxia and radiological insults all lead to ARDS and undoubtedly involve GSH deficiency, oxidative stress and accelerated lung and systemic inflammatory responses. Again, because NAC and ERGO can correct a fundamental putatively universal abnormality, the invention holds promise not only for treating patients exposed to all ARDS-inciting insults including but not limited to CDC Category A-C pathogens and other infections but also for treating patients who are exposed to any relevant insults and especially Weapons of Mass Destruction (WMD) insults. In addition, because a terrorist attack might involve one or perhaps more than one immediately definable insult, we need a safe, universal protection option to treat and prevent ARDS from all causes.

Because both NAC and ERGO are safe and can both be given orally, the invention also offers the possibility of using NAC and/or ERGO in pretreatment to large numbers of potentially exposed individuals before symptoms develop. Obviously, a major concern arises if thousands of individuals are exposed simultaneously and unexpectedly. In this event, there would not be enough ICU beds available and likewise it would be impossible to obtain diagnostic tests on all of these individuals in a timely fashion. Administering safe, orally active interventions, like NAC. and ERGO, provides a reasonable presumptive approach at mitigating ARDS and other serious sequelae following a mass tragedy. NAC and/or ERGO may even be given by "first responders" in non-clinical settings to prevent the development of ARDS.

NAC and ERGO target a specific abnormality (GSH deficiency, oxidative stress) in patients with and at-risk for ARDS. Accordingly, these interventions might be useful in combination with other interventions designed to target other specific abnormalities such as interventions directed at the invading microorganisms themselves or interventions which specifically counter other exaggerated detrimental immune or inflammatory reactions.

Both NAC and ERGO are relatively inexpensive. In addition, both interventions have long shelf-lives and do not require refrigeration. As a result, they can be stored in convenient central areas and large quantities can be moved to critical civilian or military sites very rapidly both within and outside of the United States.

When administered or co-administered, the compounds of the present invention are given in a therapeutically effective amount to the subject. As used herein, the phrase "therapeutically effective amount" means an amount that has any beneficial effect in treating the syndrome, condition or membrane injury. Determining the therapeutically effective amount of the active compound of the present invention is a matter of routine optimization and titration in the art and may depend upon such factors including, but not limited to, the extent of the condition, syndrome or injury to be treated, the age and condition of the subject to be treated, etc. Further, determining the therapeutic index of the active compounds is also a matter of routine optimization and titration in the art. The term "therapeutic index" or "therapeutic window" refers to the ratio of the dose of a drug or prodrug that produces a therapeutically beneficial response relative to the dose that produces an undesired response such as death, an elevation of markers that are indicative of toxicity, and/or pharmacological side effects.

The compounds of the present invention are administered to the subject in a pharmaceutically acceptable carrier, adjuvant or vehicle. Select examples of pharmaceutically acceptable carriers, adjuvants and vehicles, which are well-known in the art, are disclosed in *Remington: The Science and Practice of Pharmacy,* 21st Ed., Hendrickson, R., et al., Eds., Lippincott Williams & Wilkins, Baltimore, Md. (2006), which is incorporated by reference. The selection of the pharmaceutically acceptable carrier, adjuvant or vehicle will depend on a variety of factors that include, but are not limited to, the route of administration, dosage levels, the age, weight or condition of the subject, etc.

The pharmaceutical compositions of the present invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions. Such compositions also include liposomal compositions as drug carriers.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include, for example, vegetable oils, waxes, fats, semi-solid, or liquid polyols etc. For the preparation of solutions and syrups, excipients which may be used include for example water, polyols and sugars. Specific examples of excipients include, but are not limited to, poly-ethylene glycol (PEG), dimethyl sulfoxide (DMSO), ethanol and mixtures thereof. For the preparation of suspensions, oils, e.g. vegetable oil, may be used to provide oil-in-water or water-in-oil suspensions. In certain situations, delayed release preparations may be advantageous and compositions which can deliver, for example, ergothioneine or a derivative thereof in a delayed or controlled release manner may also be prepared. Prolonged gastric residence brings with it the problem of degradation by the enzymes present in the stomach and so enteric-coated capsules may also be prepared by standard techniques in the art where the active substance for release lower down in the gastro-intestinal tract.

Pharmaceutical compositions adapted for transdermal administration may be presented as discrete patches intended to remain in intimate contact with the epidermis of the recipient for a prolonged period of time. For example, the active ingredient may be delivered from the patch by ionophoresis as generally described in Pharmaceutical Research, 3(6):318 (1986).

Pharmaceutical compositions adapted for topical administration may be formulated as ointments, creams, suspensions, lotions, powders, solutions, pastes, gels, sprays, aerosols, or oils. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for nasal administration wherein the carrier is a solid include a coarse powder having a particle size for example in the nanometer range up to the micron range. For example, particles may be in the range of about 20 to about 500 microns, which is administered in the manner in which snuff is taken, i.e., by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, supercritical fluid aerosolizations, nebulizers or insufflators.

Pharmaceutical compositions adapted for parenteral administration include aqueous and non-aqueous sterile injection solution which may contain antioxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets. The pharmaceutical compositions may contain preserving agents, solubilising agents, stabilising agents, wetting agents, emulsifiers, sweeteners, colorants, odorants, salts (substances of the present invention may themselves be provided in the form of a pharmaceutically acceptable salt), buffers, coating agents or antioxidants.

The present invention also relates to methods of screening candidate compounds for their ability to mitigate the effects of alveolar capillary membrane injury. As used herein, a "candidate compound" is a compound that may be useful for treating ACMI or symptoms of ACMI, or that may be useful as a preventative of ACMI. Accordingly, the phrase "mitigate the effects" is intended to mean a reduction in the frequency or severity of ACMI or symptoms thereof. The candidate compounds can thus be screened for their ability to reduce the severity of the symptoms associated with ACMI, and they may also be screened for their ability to prevent ACMI.

The screening methods comprise stimulating a control and experimental population of cells or animal models of alveolar capillary membrane injury in the presence of either a control substance or the candidate compound, respectively, with the stimulus being capable of producing injury and/or markers of inflammatory acute lung injury in the two groups of cells. In one embodiment, the control substance is an inert substance, such as a buffer or saline solution. In other embodiment, the control compound is ergothioneine, where the candidate compound is being compared to ergothioneine for its ability to treat or prevent ACMI. Any reduction in the degree, severity, frequency and/or length etc., of injury and/or markers of alveolar capillary membrane injury in the experimental group of cells over the control group would indicate that the candidate compound may be useful for mitigating one or more of the symptoms of alveolar capillary membrane injury. The differences in the levels of markers of ACMI may be relative, absolute or normalized etc., provided that a difference can be assessed by one of skill in the art. The differences in markers of alveolar capillary membrane injury may be equal to zero, indicating that there is no difference in the candidate compound and ergothioneine, if for example, ergithioneine is being used as the control. The difference may simply be, for example, a measured fluorescent value, radiometric value, densitometric value, mass value etc., without any additional measurements or manipulations. Alternatively, the difference may be expressed as a percentage or ratio of the measured value to a measured value of another compound including, but not limited to, a standard. The difference may also be determined using in an algorithm, wherein the raw data is manipulated.

To determine the efficacy of a candidate compound to treat or prevent ACMI or symptoms thereof, the methods comprise administering the candidate compound to a group of cells or animal models and then stimulating the cells and/or animal models with a stimulus designed to produce injury or the expression and/or release of markers of ACMI. Stimuli associated with ACMI are well known in the art and include, but are not limited to, administering or insufflating interleukin-1 (IL-1) and/or interferon gamma (IFN-γ), endotoxin or lipopolysachharide (LPS) given intravenously or by aerosol administration, oleic acid, and hyperoxia and chemical agents such as phorbol myristate acetate (PMA), intestinal ischemia-reperfusion, aspiration, gastric contents or HCL insufflation, cecal ligation and puncture, hypoxia followed by reoxygenation, barotrauma/ventilator lung, chlorine gas, hemorrhagic shock, fracture and hypochlorite insufflation to the cells or subjects. The stimulated cells may be in an in vitro setting, or the cells may be in an in vivo setting where the cells are part of a test subject. When performed in an in vitro setting, the type of cultured cells include, but are not limited to, epithelial cells, endothelial cells, squamous cells, polymorphonuclear (PMN) cells (neutrophils, basophils, eosinophils) moncytes, macrophages, etc.

Markers of ACMI are well-known in the art and include, but are not limited to, the presence or production of inflammatory cytokines. Examples of inflammatory cytokines include, but are not limited to, interleukin-1 (IL-1), interferon gamma (IFN-$\gamma$), tumor necrosis factor alpha (TNF-$\alpha$) and interleukin-8 (IL-8). Assaying for specific cytokines is well known in the art and includes assays such as ELISA assays, Northern blots, Western Blots, activity assays and the like. Other markers of ACMI include, but are not limited to, changes in blood pressure, increased numbers of lung neutrophils, increased levels of lung GSSG, increased concentration of expired $H_2O_2$, increased levels of lactate dehydrogenase (LDH) and a lung leak index. Other markers of ACMI can be assayed using morphologic assays of lung injury, physiologic derangements including measurements of hypoxia, and biochemical abnormalities including GSH depletion, alterations of GSH/GSSG ratios, increased measurements of oxidative stress, e.g., increased levels of 8-iso-PGF2$\alpha$. Assays for measuring each of the markers of ACMI are well-known in the art, some of which are disclosed or reviewed in Repine, J. E., Lancet, 339(8791):466-9 (1992) and Ware L. B. and Matthay M. A., N Engl J Med. 342(18): 1334-49 (2000), both of which are incorporated by reference.

The markers of ACMI may be assayed using frequency comb spectroscopy. Frequency comb spectroscopy is an innovative, powerful technique that can measure multiple molecules in exhaled gases accurately, non-invasively, simultaneously and more sensitively (in parts/billion, 3-7) than conventional single factor assays. Frequency comb spectroscopy may be used to measure a novel battery of alcohol, inflammation and oxidative stress related biomarkers in exhaled gases that will not only determine the efficacy of a candidate compound to treat or prevent ACMI or symptoms thereof, but will also indicate which ARDS patients specifically need anti-inflammatory and antioxidant therapy and help monitor the effectiveness of that specific therapy.

In one specific embodiment of the present invention, the screening methods are performed in an in vitro setting and the cultured cells are assayed for at least the production of inflammatory cytokines in response to the stimulus. In another embodiment, the screening methods are performed in subjects and the subjects are assessed for at least one of $H_2O_2$ expiration, lung LDH levels, lung leak index and lung lavage neutrophil counts, lung levels of albumin, including $^{125}I$ labeled albumin previously injected, and/or lung myelperoxidase measurements as a biochemical index of lung neutrophil numbers.

To determine if the candidate compound can be useful to treat ACMI, the candidate compound can be given after the ACMI-inducing stimulus, and the markers of ACMI can then be assessed. To determine if the candidate compound can be useful as a preventative, the candidate compound can be given before the ACMI-inducing stimulus and the markers of ACMI can be assessed after the stimulus. In one specific embodiment, the candidate compound can be co-administered with ergothioneine to the cells, to determine if the candidate compound would be useful in combination therapy.

The following examples are illustrative of select embodiments of the present invention and are not meant to limit the scope of the invention.

EXAMPLES

Example 1

NAC Treatment Decreases Lung Injury in Cytokine Insufflated Rats (4).

Figure 1B:
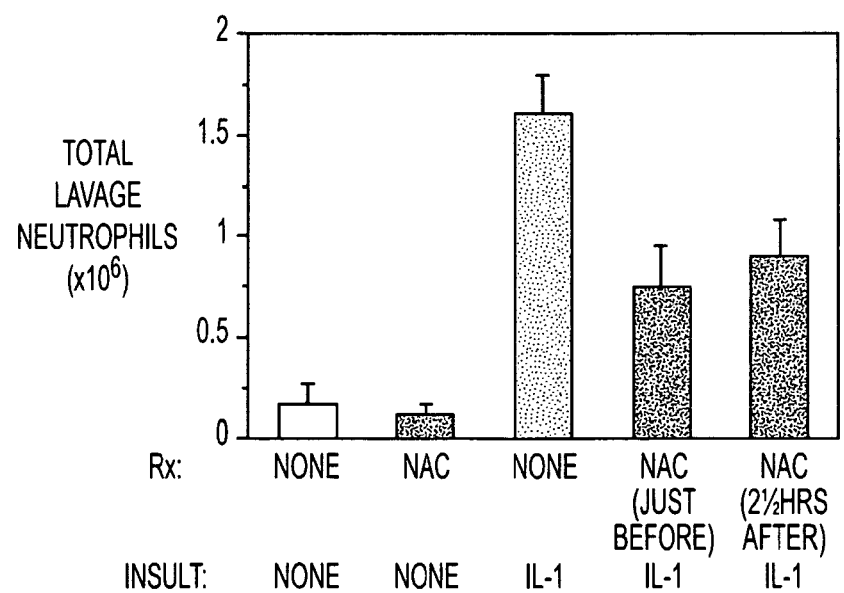
Figure 1C:
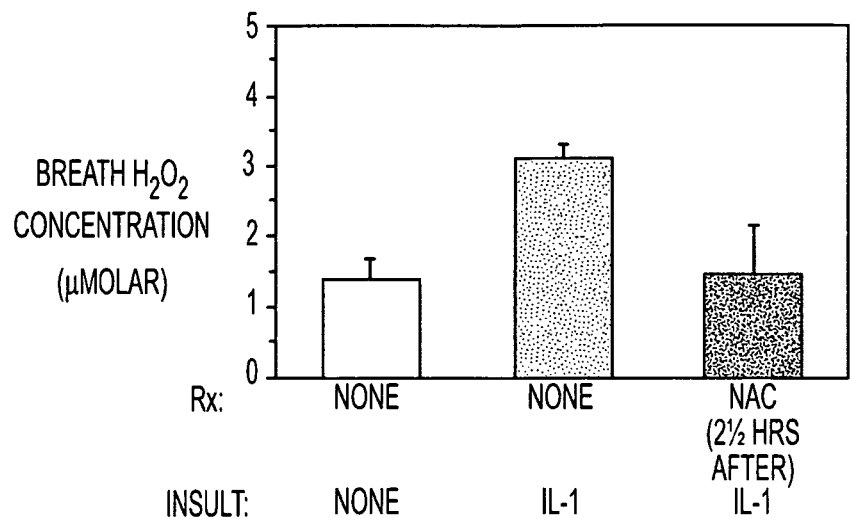
Figure 1D:
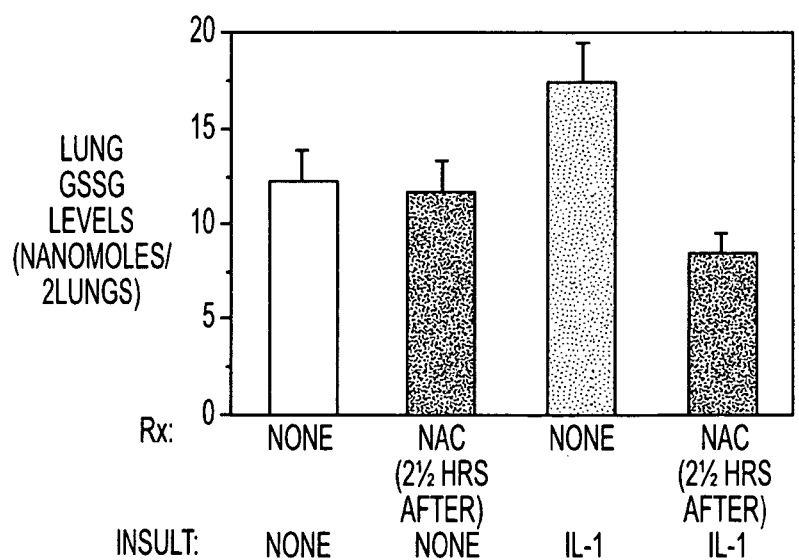

Insufflating IL-1 produced an inflammatory acute lung injury (ARDS, FIG. 1A) in rats 5 hours later, which was associated with increases in lung lavage neutrophils (FIG. 1B), expired $H_2O_2$ levels (FIG. 1C) and lung GSSG levels (FIG. 1D). In contrast, rats administered NAC (150 mg/kg intravenously) either just before or 2½ hours after IL-1 insufflation had decreased lung leak index, lung lavage neutrophil numbers, expired $H_2O_2$ levels and lung GSSG levels compared to untreated rats insufflated with IL-1. The results confirm that NAC alone may be useful as a preventative or treatment for ACMI in subject.

Example 2

ERGO Pre-treatment Decreases Lung Injury and Inflammation in Lungs of Cytokine Insufflated Rats.

Figure 2A:
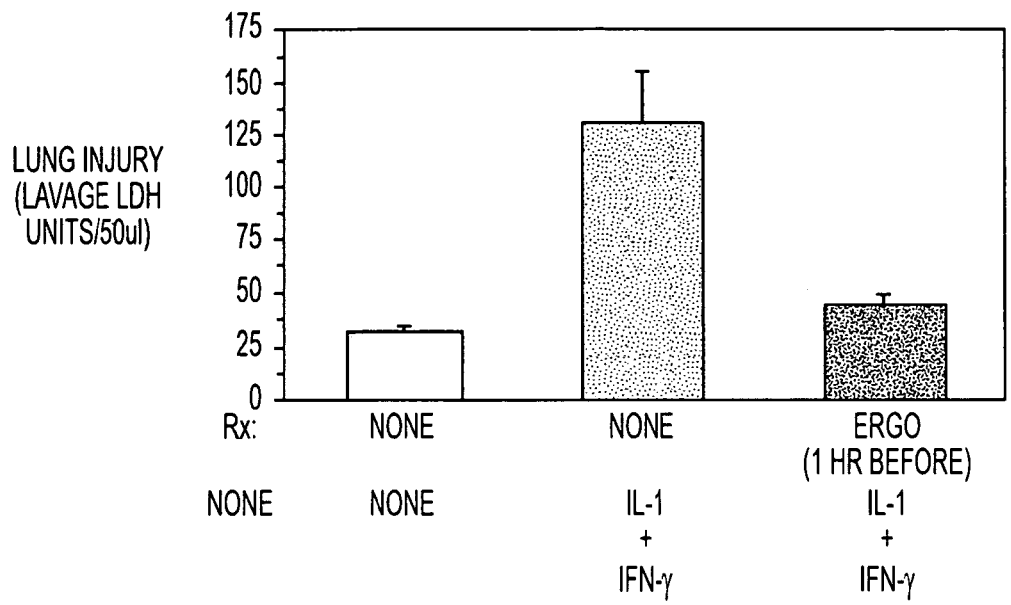
FIG. 2 depicts the ability of L-ergothioneine to prevent inflammatory acute lung injury mediated by interleukin 1 (IL-1) and interferon gamma (IFN-$\gamma$).
Figure 2B:
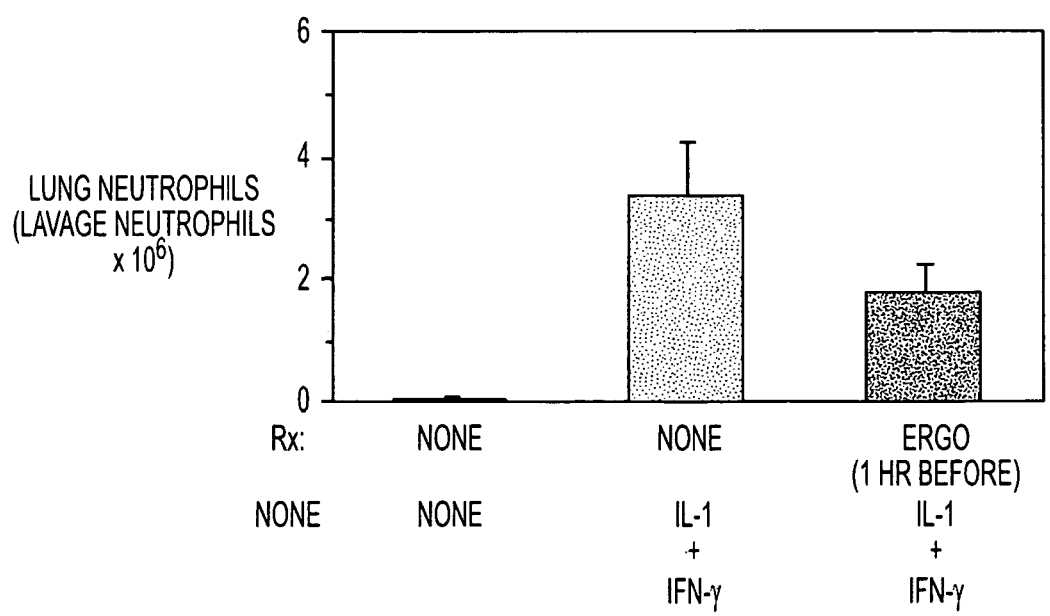

Insufflating IL-1 and interferon-$\gamma$ (IFN-$\gamma$) produced an inflammatory acute lung injury (ARDS) in rats 24 hours later (9). Cytokine insufflated rats had increased lung lavage LDH concentrations (FIG. 2A) and neutrophil numbers (FIG. 2B) compared to saline insufflated control rats. In contrast, rats administered (Rx) a single intravenous injection of 150 mg/kg ERGO (1 hour before) IL-1 and IFN-$\gamma$ insufflation showed reduced levels of markers of alveolar capillary membrane injury by exhibiting decreased lung lavage LDH, total leukocyte and neutrophil concentrations. Lavage LDH levels paralleled other measures of lung injury including increased epithelial-derived cytokeratin 18 and endothelial-derived angiotensin converting enzyme (ACE) levels and morphologic evidence of inflammation and injury.

Example 3

ERGO Treatment (150 mg/kg Given 1 Hour Before Cytokine Insufflation) After Insult Decreases Injury and Inflammation in Lungs of Cytokine Insufflated Rats.

Figure 3A:
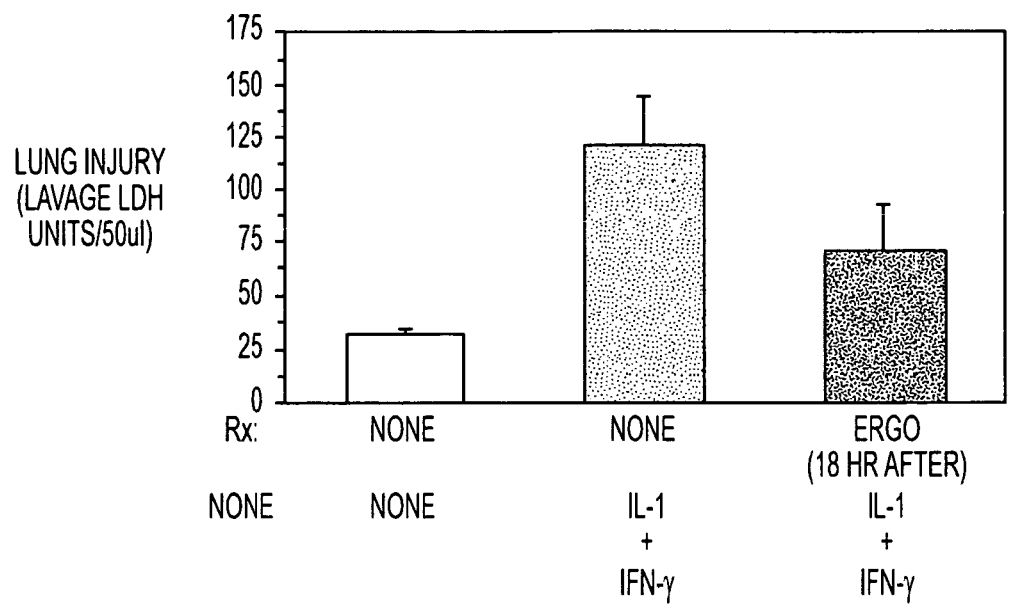
FIG. 3 depicts the ability of L-ergothioneine to mitigate inflammatory acute lung injury mediated by interleukin 1 (IL-1) and interferon gamma (IFN-$\gamma$).
Figure 3B:
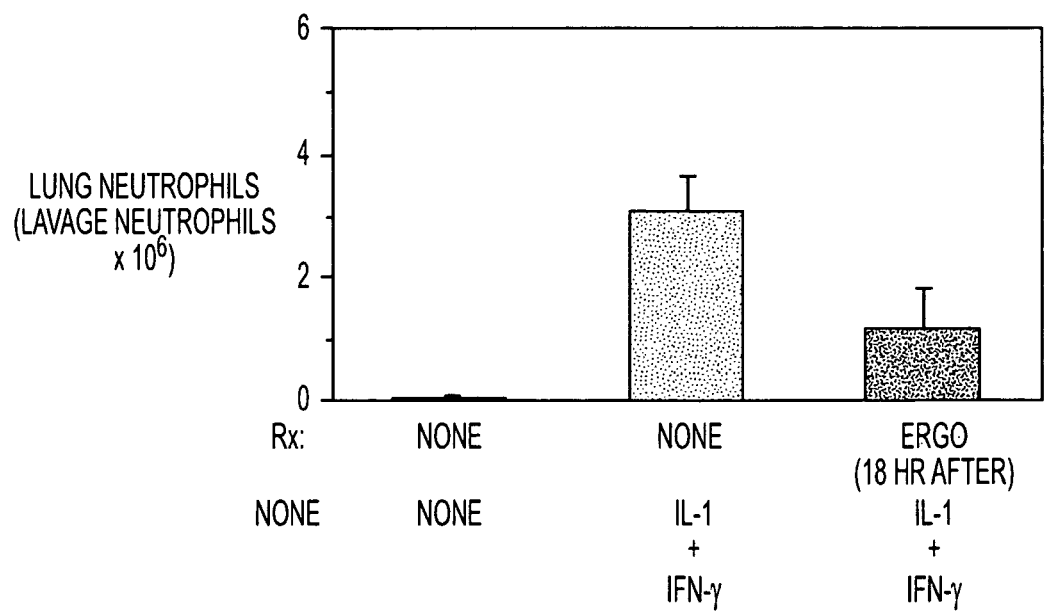

Rats administered a single intravenous bolus of 150 mg/kg ERGO (18 hours after) cytokine insufflation exhibited a reduction in the severity of markers of alveolar capillary membrane injury (FIG. 3A) lung inflammation (data not shown) and lung neutrophil numbers (FIG. 3B) compared to saline insufflated untreated rats insufflated with cytokines. Remarkably, protection occurred with ERGO administered post-insult even after some neutrophils had invaded the lung.

Example 4

ERGO Treatment (15 mg/kg Given 1 Hour before Cytokine Insufflation) After Insult Decreases Injury and Inflammation in Lungs of Cytokine Insufflated Rats.

Figure 4A:
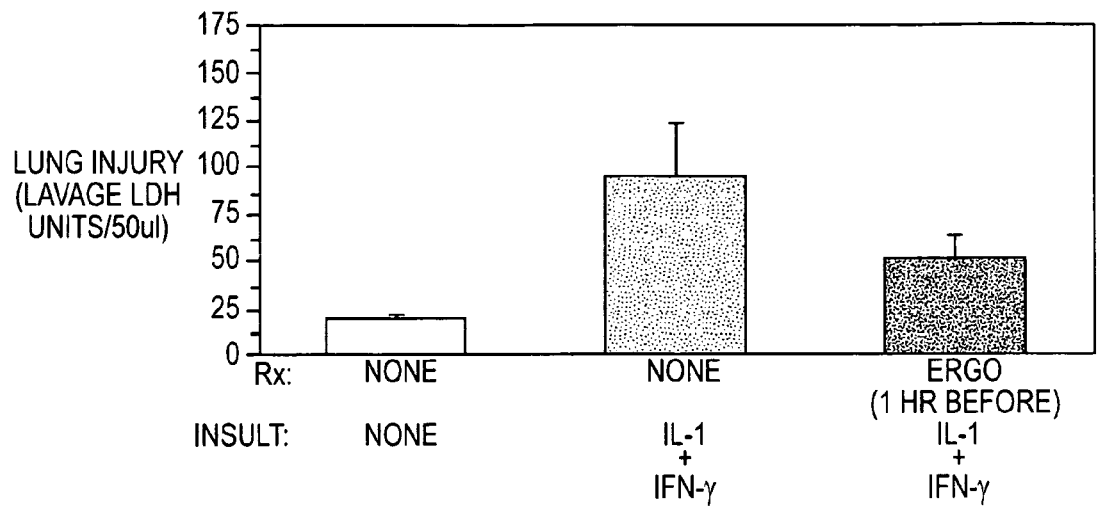
FIG. 4 depicts the ability of L-ergothioneine to prevent inflammatory acute lung injury mediated by interleukin 1 (IL-1) and interferon gamma (IFN-$\gamma$).
Figure 4B:
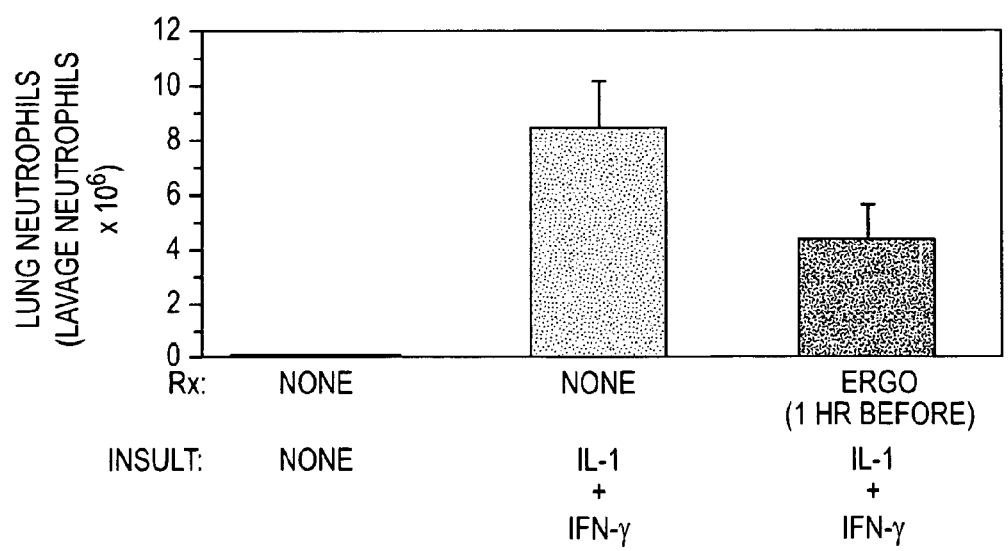

Rats were administered a single intravenous bolus of 15 mg/kg ERGO (given 1 hour before) cytokine insufflation developed less lung injury (FIG. 4A) and lung neutrophils (FIG. 4B) than untreated rats insufflated with cytokines. Each value is the mean +/−SEM of 3 to 6 determinations. Protection using a much lower dose of ERGO (1/10 of the initial test dose) suggested a large therapeutic range for the effectiveness of ERGO as a potential way to treat and prevent ARDS.

What is claimed is:

1. A method of treating a subject with alveolar capillary membrane injury where the alveolar capillary membrane injury is a symptom of acute respiratory distress syndrome (ARDS), the method comprising administering in vivo to the subject in need of such treatment a therapeutically effective amount of ergothioneine and a pharmaceutically acceptable carrier.

2. The method of claim 1, further comprising administering to the subject a therapeutically effective amount of a compound selected from the group consisting of N-acetyl-cysteine (NAC) and alpha-lipoic acid; and a pharmaceutically acceptable carrier.

3. The method of claim 2, wherein the NAC or the alpha-lipoic acid is administered at the same time as the ergothioneine.

4. The method of claim 2, wherein the NAC or the alpha-lipoic acid is administered after the ergothioneine.

5. The method of claim 2, wherein the NAC or the alpha-lipoic acid is administered before the ergothioneine.

6. The method of claim 2, wherein ergothioneine and NAC are administered to the subject.

7. The method of claim 2, wherein ergothioneine and alpha-lipoic acid are administered to the subject.

8. A method of treating a subject with alveolar capillary membrane injury where the alveolar capillary membrane injury is a symptom of a condition selected from the group consisting of infant respiratory distress syndrome, sepsis, lung trauma and pulmonary infection, the method comprising administering in vivo to the subject in need of such treatment a therapeutically effective amount of ergothioneine and a pharmaceutically acceptable carrier.

9. The method of claim 8, further comprising administering to the subject a therapeutically effective amount of a compound selected from the group consisting of N-acetyl-cysteine (NAC) and alpha-lipoic acid; and a pharmaceutically acceptable carrier.

10. The method of claim 9, wherein the NAC or the alpha-lipoic acid is administered at the same time as the ergothioneine.

11. The method of claim 9, wherein the NAC or the alpha-lipoic acid is administered after the ergothioneine.

12. The method of claim 9, wherein the NAC or the alpha-lipoic acid is administered before the ergothioneine.

13. The method of claim 9, wherein ergothioneine and NAC are administered to the subject.

14. The method of claim 9, wherein ergothioneine and alpha-lipoic acid are administered to the subject.

* * * * *